US011173025B2

(12) United States Patent
Antonio Lourenco

(10) Patent No.: US 11,173,025 B2
(45) Date of Patent: Nov. 16, 2021

(54) SYSTEM FOR BRANCHES FOR ENDOVASCULAR ENDOPROSTHESES AND CORRESPONDING ENDOPROSTHESIS FOR ENDOVASCULAR TREATMENT OF AORTIC ANEURYSMS OR DISSECTIONS

(71) Applicant: Merit Medical Systems, Inc., South Jordan, UT (US)

(72) Inventor: Marco Antonio Lourenco, Curitiba (BR)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 16/320,659

(22) PCT Filed: May 29, 2017

(86) PCT No.: PCT/BR2017/050134
§ 371 (c)(1),
(2) Date: Jan. 25, 2019

(87) PCT Pub. No.: WO2018/018114
PCT Pub. Date: Feb. 1, 2018

(65) Prior Publication Data
US 2019/0159886 A1 May 30, 2019

(30) Foreign Application Priority Data
Jul. 29, 2016 (BR) .......................... 102016017768-5

(51) Int. Cl.
*A61F 2/07* (2013.01)
*A61F 2/848* (2013.01)
*A61F 2/86* (2013.01)
*A61F 2/89* (2013.01)
*A61F 2/06* (2013.01)

(52) U.S. Cl.
CPC ................ *A61F 2/07* (2013.01); *A61F 2/848* (2013.01); *A61F 2/86* (2013.01); *A61F 2/89* (2013.01); *A61F 2002/061* (2013.01); *A61F 2002/065* (2013.01); *A61F 2002/075* (2013.01)

(58) Field of Classification Search
CPC .. A61F 2/954; A61F 2/07; A61F 2/848; A61F 2220/075
USPC ................................................ 623/1.35–1.48
See application file for complete search history.

(56) References Cited

U.S. PATENT DOCUMENTS

2005/0131518 A1* 6/2005 Hartley ................... A61F 2/856
623/1.13
2009/0125095 A1 5/2009 Bui et al.
(Continued)

FOREIGN PATENT DOCUMENTS

BR 2015-43322 C * 1/2017 ............... A61F 2/07
WO 2015109375 A1 7/2015

*Primary Examiner* — Suzette J Gherbi
(74) *Attorney, Agent, or Firm* — Stoel Rives LLP

(57) ABSTRACT

An internal duct and fixing system for branches for endovascular endoprostheses, and a corresponding endoprosthesis, for endovascular treatment of aneurysms or dissections of the aorta, including (i) an endoprosthesis provided with windows, (ii) one or more occlusions, fixed to the endoprosthesis by a suture, reversibly occluding the windows, and a set of fixing and duct elements that forms one or more internal channels of the endoprosthesis, preferably in the region adjacent to one of the windows.

15 Claims, 3 Drawing Sheets

(56) References Cited

U.S. PATENT DOCUMENTS

| | | | |
|---|---|---|---|
| 2011/0046720 A1* | 2/2011 | Shalev | A61F 2/07 623/1.18 |
| 2012/0191180 A1* | 7/2012 | Hartley | A61F 2/856 623/1.35 |
| 2012/0221096 A1 | 8/2012 | Roeder et al. | |
| 2012/0323307 A1* | 12/2012 | Richter | A61F 2/89 623/1.16 |
| 2013/0053945 A1* | 2/2013 | Greenberg | A61F 2/954 623/1.12 |
| 2013/0197622 A1* | 8/2013 | Mitra | A61F 2/2409 623/1.15 |
| 2014/0180393 A1* | 6/2014 | Roeder | A61F 2/07 623/1.15 |
| 2014/0371836 A1* | 12/2014 | Silveira | A61F 2/07 623/1.2 |
| 2016/0106538 A1* | 4/2016 | Mitra | C08L 33/02 623/1.11 |
| 2016/0310258 A1* | 10/2016 | Wang | A61F 2/844 |
| 2016/0361153 A1* | 12/2016 | Shahriari | A61F 2/89 |
| 2017/0049588 A1* | 2/2017 | Davis | A61F 2/07 |
| 2017/0252145 A1* | 9/2017 | Roeder | A61F 2/07 |
| 2018/0228592 A1* | 8/2018 | Eaton | A61F 2/07 |
| 2018/0243076 A1* | 8/2018 | Greenberg | A61F 2/856 |
| 2019/0030462 A1* | 1/2019 | Masten, Jr. | B01D 21/265 |
| 2020/0138560 A1* | 5/2020 | Karavany | A61F 2/06 |
| 2020/0138561 A1* | 5/2020 | Douthitt | G16H 30/20 |

* cited by examiner

SYSTEM FOR BRANCHES FOR ENDOVASCULAR ENDOPROSTHESES AND CORRESPONDING ENDOPROSTHESIS FOR ENDOVASCULAR TREATMENT OF AORTIC ANEURYSMS OR DISSECTIONS

FIELD OF APPLICATION

The present invention belongs to the field of prostheses implantable within the human body, especially to the field of devices that prevent collapsing of tubular structures of the body, such as endoluminal vascular prostheses or coated endoprostheses stent graft.

INTRODUCTION

The present invention relates to an internal duct and fixing system for branches for endovascular endoprostheses and a corresponding endoprosthesis for endovascular treatment of aortic aneurysms or dissections, especially of aneurysms or dissections located at emergency sites and/or confluence of important arterial branches.

STATE OF THE ART

Endovascular treatment of aneurysm or aortic dissection is accomplished by the implantation of a coated vascular endoprosthesis or stent graft which, in general, is a tubular device formed by a synthetic material that covers it, being supported by a supporting structure that confers it shape and resilience.

An aortic aneurysm is a protrusion—swelling—"on the aortic artery wall, possibly anywhere along it, but usually in a weakened part. Often, a blood clot or thrombus forms inside the aneurysm, which can spread throughout the entire wall.

A dissection of the aorta, also called aortic dissecting aneurysm, is an often fatal condition in which the internal coating of the aortic wall suffers a laceration, while the external coating remains intact, a passage of blood through laceration occurs, with dissection—separation—of the middle layer and the creation of a new canal in the aorta wall.

The endoprosthesis is arranged within the artery in order to exclude or isolate the aneurysmal sac or dissection region, thereby restoring normal blood flow to the compromised artery.

However, the incidence of aneurysms or dissections in regions where there are vital branches in the aorta makes it difficult to implant conventional endoprostheses, "shelf products" available in the medical devices market. The vital ramifications cannot be obstructed, since this would cause insufficiency of organs or regions irrigated by these vital branches.

Several types of endoprostheses for the treatment of aneurysms in critical regions, such as endoprostheses with fenestrations, for treating aneurysms of the just-renal abdominal aorta (near the kidney circulation) are available on the market. These endoprostheses have fenestrations or openings especially provided to allow the passage of blood flow to the renal arteries and, in some cases, to the superior mesenteric artery, depending on the impairment caused by the aneurysm. These endoprostheses, however, have several anatomical limitations: most of the time they need to be customized due to the different anatomical types of the aneurysms, the height and angulation of the visceral vessel emergency in relation to the other vessels and/or the need for revascularization of 1, 2, 3 or 4 visceral vessels. In addition, it must be remembered that the difficulty of selectivation of the visceral vessels may occur due to tortuosity of the aorta.

There are also branched endoprostheses, with branches partially internal and external and sometimes totally external. Depending on the individual anatomy of the patient, these endoprostheses are customized, which requires a waiting period of a few weeks, which can significantly delay the surgery.

One of the so-called "universal" endoprostheses currently available on the market is the endoprosthesis Zenith t-Branch, by Cook Medical, which, according to the manufacturer, is a device "off-the-shelf", that is, for use in the majority of patients with thoracic-abdominal aneurysm, even with different anatomies and without the need to wait for customization. However, it has been observed that the device Zenith t-Branch has the disadvantage of serving only when one has the 4 pervious visceral branches to be revascularized. It has its introducer with a great caliber profile 22 Fr(OD), which makes difficult the passage of the device in femoral and iliac arteries of small caliber. It has only one configuration and arrangement of the 4 branches, so, it can not be modified.

The company W. L. GORE & ASSOCIATES, INC. is in the stage of human trials of an endoprosthesis for the treatment of thoracic-abdominal aneurysms, with 4 internal branches made of the endoprosthesis fabric (polytetrafluoroethylene or PTFE), 2 being in the upper position and 2 in the lower position.

Part of this solution of a system of internal branches made with the endoprostheses fabric itself, for attachment or connection of stents that will revascularize the visceral vessels, can be found in patent documents WO 2013/025727 (A1) and U.S. Pat. No. 8,945,200 (B1). W. L. GORE & ASSOCIATES, INC. intends that this endoprosthesis is a "shelf" product and that it will therefore compete with the endoprosthesis Zenith t-Branch by Cook Medical. Its disadvantages, however, are practically the same as those of its competitor. It can be used only when the 4 pervious visceral branches are used to be revascularized. It has only one configuration and arrangement of the 4 branches, which cannot be modified. The internal branches comprise a PTFE and metal skeleton, stent type, as well as including a large amount of internal material to form these branches, increasing the profile of the implanter and making it difficult to implant it in patients with femoral arteries and small caliber iliac arteries.

There are other patent documents relating to this subject matter which reveal one or more internal channels with metallic stents with or without fabric coating (polyester or PTFE) for fixing or connecting the endoprostheses that will revascularize the visceral vessels. Some examples of this type of solution are disclosed by documents U.S. Pat. No. 6,645,242 (B1), WO 2010/024879 (A1), WO 201371222 (A1), US 2007/0233220 (A1), US 2008/0269866 (A1) and US 2011/257731 (A1).

This type of device requires a large amount of material (metal and/or fabric) for the formation of the channels, which results in a great caliber endoprosthesis, making the implantation difficult in patients with smaller caliber access(es). If they are customized, they will have the same disadvantage mentioned above regarding the important delay for their preparation and the consequent delay in performing the surgery. If they are intended to serve as a "shelf product", they will end up having a unique configuration, causing a limitation in relation to the anatomy of each patient (need for the 4 visceral vessels to be pervious and obligatory revascularization of the 4 visceral vessels). The final cost of these devices will also be high due to the material required for its making.

Malina et al. (Malina M. et al., "*EVAR and complex anatomy: An update on fenestrated and branched stent grafts*", 2008, Scandinavian Journal of Surgery, n. 97: 195-204, 2008) estimate that 20% of the patients who develop aortic aneurysms have abdominal aortic aneurysm neck morphologies that are not appropriate for the use of standard or conventional endoprostheses, needing to cross the visceral branches to achieve an efficient endoprosthesis sealing, ie, the isolation of the aneurysm.

Tsilimparis et al. (Tsilimparis, N. and Ricotta II, J. J., "*Type IV thoracic-abdominal Aneurysms: What's Next?*", 2012, Endovascular Today, March.) corroborate the estimates of Malina et al, noting that 20% of patients with aortic aneurysms cannot be treated with the commercially available devices because the aneurysm compromises the visceral branches.

Accordingly, Murphy et al. (Murphy, E. H. et al., "*Fenestrated Endografting for the Treatment of Descending Thoracic Aneurysms*", 2009, Endovascular Today, January, pp 26-33.) claim that more than 20% of patients with abdominal aortic aneurysms could avoid open surgery and benefit from endovascular treatment if there were devices that could be used over vital branches.

Efforts have been made to overcome these limitations by embedding fenestrations (windows or openings) or branches in the endoprostheses during the manufacturing process—see Anderson (Anderson, J. L., "*Fenestrated and branch aortic stent grafts*" Endovascular Today, April 2004, pp. 40-46) and Stanley et al. (Stanley, B. M.; Semmens, J. B.; Lawrence-Brown, M. M. D.; Goodman, M. A. e Hartley, D. E., "*Fenestration in endovascular grafts for aortic aneurysm repair: new horizons for preserving blood flow in branch vessels*", J. Endovasc. Ther., 2001, v. 8, pp. 16-24).

Despite the satisfactory results, these devices require a high degree of customization, taking into consideration the anatomy of each patient, which significantly increases the production cost of these devices and the waiting time to perform the procedure, since they must be produced on demand.

A technical solution found for the maintenance of the vital branches of the aorta artery is described by Kasirajan (Kasirajan, K., "*Tandem Endografts for Type II TAAAs*", 2011, vol. 10, n. 5, pp. 30-34.) through the treatment of a thoracic-abdominal aortic aneurysm using numerous commercial (off-the-shelf) endoprostheses. Kasirajan (2011) utilizes a technique using arterial endoprostheses simply connected (one inside the other) or connected in parallel, i.e., by placing one or two endoprostheses in parallel inside another straight or bifurcated arterial endoprosthesis.

According to Lobato et al. (Lobato, A. C. et al., "*The sandwich technique: how to make it work for thoracic-abdominal aneurysm exclusion*", Journal of Vascular and Endovascular Surgery, 2011, vol. 18, pp-1-2.) e Kolvenbach et al. (Kolvenbach, R. R. et al., "*Urgent Endovascular Treatment of Thoraco-abdominal Aneurysm Using a Sandwich Technique and Chimney Grafts—A Technical Description*", European Journal of Vascular Surgery, 2010, xx, pp. 1-7.), the use of endoprostheses in parallel (chimney, snorkel and sandwich) has been disseminated as a possible solution for the cases of extreme urgency because they make use of conventional commercial (off-the-shelf) endoprostheses.

However, as Tsilimparis and Ricotta II (2012) highlight, there are no medium or long-term data confirming the effectiveness of these types of techniques, making its use in elective procedures still questionable in the medical area. Malina et al. (2008) warn that the in parallel technique chimney, when used in long lengths, can generate great channels between endoprostheses causing Type I endoleak.

Efforts in addressing the treatment both of aortic arch aneurysms and thoracic-abdominal aneurysms were made by Chuter (WO2005027784), which aims to build already branched endoprostheses without the need for customization. As described by Chuter (2005) the coated endoprosthesis has small predefined branches that are extended with other endoprostheses for the maintenance of aortic vital branches. However, as Chuter (2005) describes, different configurations are needed for different regions of the aorta, in other words, the solution is not universal. Chuter (2005) also describes some configurations of solutions for endoluminais prosthesis with multiple cylindrical threads positioned in parallel within a larger cylinder, however, the cylinders are large and take a lot of internal space.

In another document, Chuter et al. (US20100312326) describe some configurations of solutions for modular bifurcated endoprostheses that are based on a cylindrical main body with internal cylinders connected and directed outwards the main cylinder turning into branches, similar to the configurations described by Greenberg (US20090048663). This solution also occupies precious internal space, making endoprostheses of this kind more difficult (perhaps impossible) to be used in patients with smaller caliber access(es).

Parodi (WO2013071222) describes, in general terms, fenestrated and branched endoprostheses called "universal" for the treatment of aortic aneurysm. According to Parodi (WO2013071222), the solution is based on different configurations of cylinders of different diameters placed side by side in parallel along the aorta axis, sharing internal and external walls, depending on the configuration (Parodi, WO2013071222, [0095] p. 20).

Parodi's solution (2013) resembles the configurations described by Greenberg et al. (US20060247761). In addition to the evident leakage problems between the laterally connected cylinders, the position of cylinders perpendicular or inclined to the movement of blood in the artery also occupies a lot of internal space.

The generic configurations of the mentioned documents present similar features based on fenestrations in the main body and branches connected to the main body used for the coupling of other coated endoprostheses and, generally, in addition to the aforementioned problems, can even cause difficulties in the surgical procedure and in the patient's recovery. Although being referred as "universal", the configurations described require accurate positioning in the connections with the visceral branches to reduce the likelihood of leaks.

Considering that there are numerous small aortic branches that keeps the blood flow also to the spinal cord, the placement of an endoprosthesis like a thoracic-abdominal one, can cause postoperative paraplegia. None of the described configurations present an alternative for reducing the risk of patient's postoperative paraplegia.

As can be inferred from the foregoing description, there is space for a coated arterial endoprosthesis which overcomes the drawbacks of the prior art and provides a device capable of serving to the treatment of aortic aneurysms or dissections as broadly as possible from the aortic arch to the thoracic-abdominal region, especially in places of emergency and/or confluence of important arterial branches, provided with a system of fixation and internal conduction of branches that allows the application also in patients with smaller caliber accesses.

OBJECTIVES OF THE INVENTION

An objective of the present invention is therefore to provide an internal duct and fixing system for branches for endovascular endoprostheses according to the features of claim 1.

Another objective of the present invention is to provide a corresponding endoprosthesis for the endovascular treatment of aortic dissections or aneurysms according to the provisions of claim X.

Other features and details of the characteristics are represented by the dependent claims numbered Y to Z.

BRIEF DESCRIPTION OF THE DRAWINGS

For better understanding and visualization of the object of the present invention, the same will now be described with reference to the attached drawings, representing the technical effect obtained by means of an exemplary embodiment not limiting the scope of the present invention, wherein.

DETAILED DESCRIPTION OF THE INVENTION

Figures 1A, 1B:
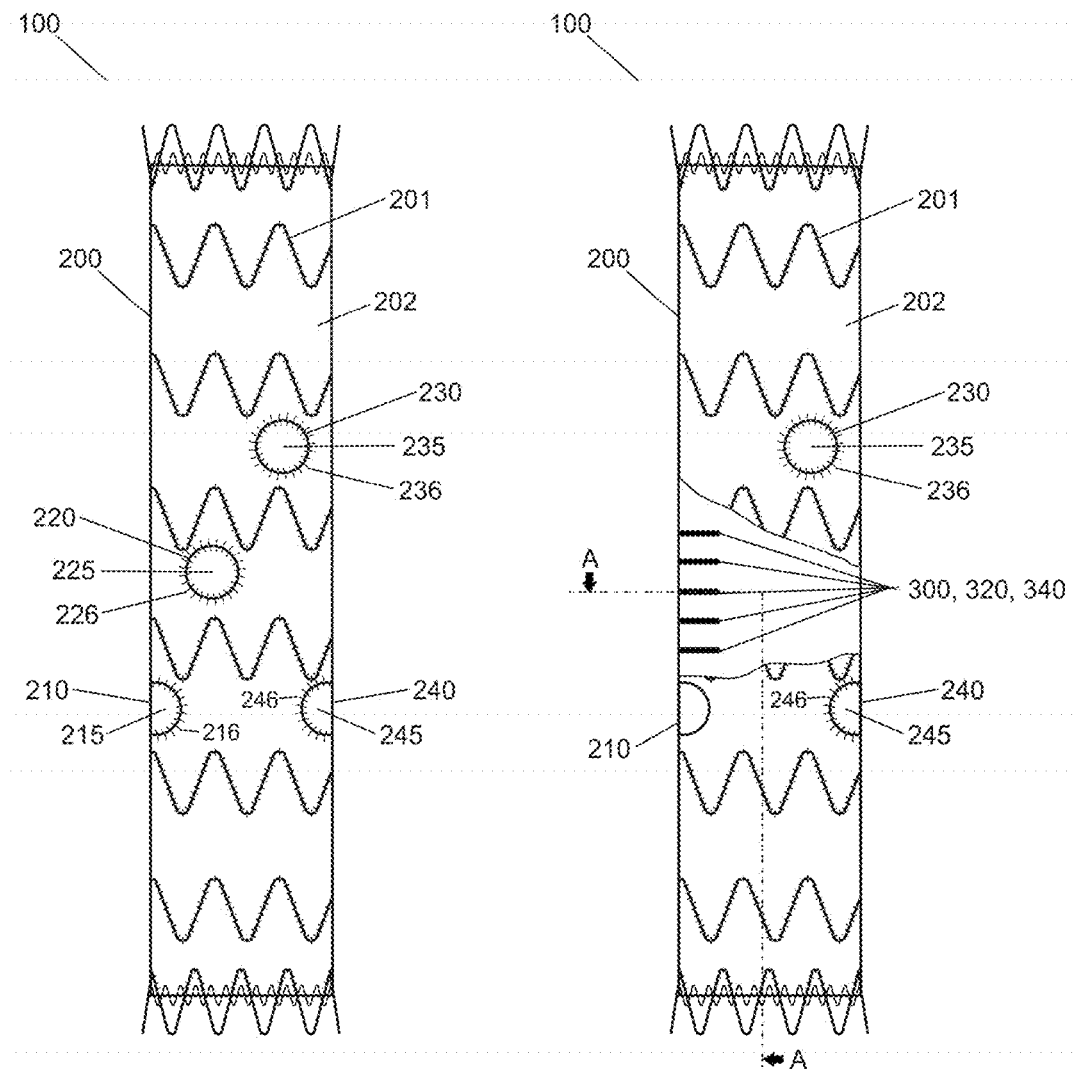
FIG. 1a: schematically shows a side view of an internal duct and fixing system for branches for endovascular endoprostheses according to the invention.
FIG. 1b: schematically shows a partial section view of the endoprosthesis of FIG. 1a, partially showing its interior.
Figure 1C:
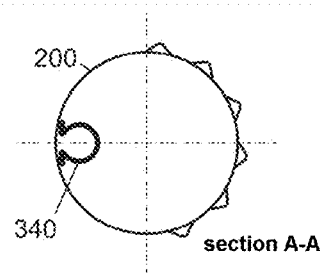
FIG. 1c: schematically shows a top view of the cutting line A-A of FIG. 1b.

The present invention will be now described in detail based on the figures above, but without limiting the same.
Internal Duct and Fixing System for Branches An internal duct and fixing system for branches for endovascular endoprostheses, or simply system 100 according to the invention, is a system as schematically represented by FIGS. 1a, 1b and 1c and comprising:
- (i) endoprosthesis (200) having a structure (201) and a coating (202) wherein the outer mantle of the coating (202) is provided with fenestrations (210, 220, 230, 240);
- (ii) one or more occlusions (215, 225, 235, 245), fixed to the coating (202) by means of suture (216, 226, 236, 246), reversibly occluding the fenestrations (210, 220, 230, 240), and
- (iii) a set of fixing and duct elements (300), which can be:
  - (iii-a) a set of flexible fixing and conducting arches (320), individually fixed to the coating (202); and/or
  - (iii-b) a set of rigid fixing and conducting rings (340), individually fixed to the coating (202);

The endoprosthesis (200) according to the invention comprises a structure (201) and a coating (202), the coating (202) being provided with one or more fenestrations (210, 220, 230, 240) (202), depending on the location of the aneurysm or dissection to be treated.

In a preferred embodiment of the invention, the structure (201) is made of biocompatible metallic material suitable for devices of this kind such as, but not limited to, alloys of nickel and titanium, preferably nitinol.

In another embodiment of the present invention, the coating (202) is made from biocompatible synthetic material suitable for such devices as, for example, but not limited to, polytetrafluoroethylene (PTFE) or the like.

The occlusions (215, 225, 235, 245) reversibly occlude the fenestrations (210, 220, 230, 240) by which they are previously fixed to the coating (202) by means of sutures (216, 226, 236, 246).

In another embodiment of the present invention, the occlusions (215, 225, 235, 245) are made of biocompatible synthetic material and suitable for devices of this type, such as, but not limited to, polytetrafluoroethylene (PTFE) or polyester or the like, and preferably the same material as the endoprosthesis (200).

In another embodiment of the present invention, the suture (216, 226, 236, 246) is made with surgical wire of made cardiovascular suture of, for example, but not limited to the usual and appropriate polyester fibers (Mersilene®), silk, cotton and other usual and appropriate materials.

The set of fixing and duct elements (300) forms one or more internal channels of the coating (202), being therefore fixed to the internal wall of the coating (202), preferably in the region adjacent one of the fenestrations (210, 220, 230, 240).

The set of fixing and duct elements (300) can be constructed from flexible fixing and conducting arches (320), formed with flexible filamentary material suitable for such procedures. The filamentary material may be cardiovascular surgical suture made from, for example, but not limited to, polyester fibers (such as Mersilene®), silk and other usual and suitable materials.

Figure 2:
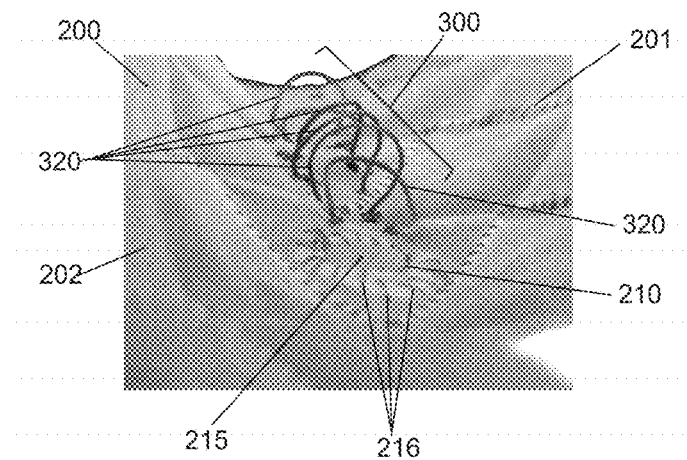
FIG. 2: shows a digital image of an internal part of an endoprosthesis of the system according to the invention.

FIG. 2 shows the digital image of an endoprosthesis (200) according to the invention, in which a set of fixing and duct elements (300) in the form of flexible fixing and conducting arches (320), forms an internal channel starting from one of the fenestrations (210) still closed by an occlusion (215) fixed by a suture (216) to the internal wall of the structure (202) of the endoprosthesis (200).

Figure 3:
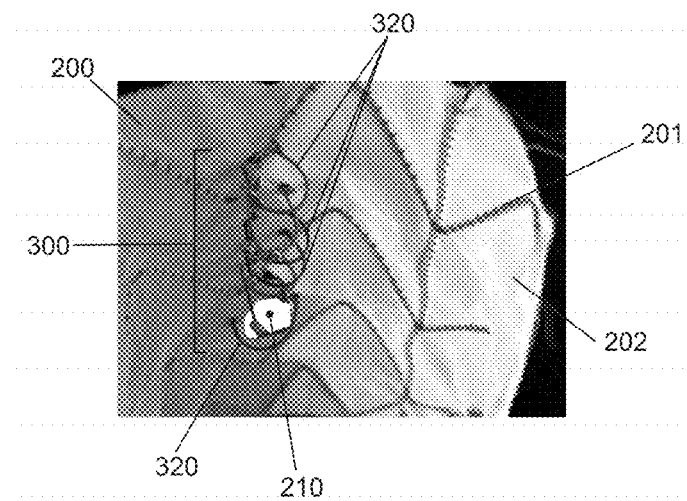
FIG. 3: shows a digital image of an internal part of an endoprosthesis of the system according to the invention.

FIG. 3 shows the digital image of the endoprosthesis (200) of FIG. 2 with the occlusion (215) removed.

Figure 4:
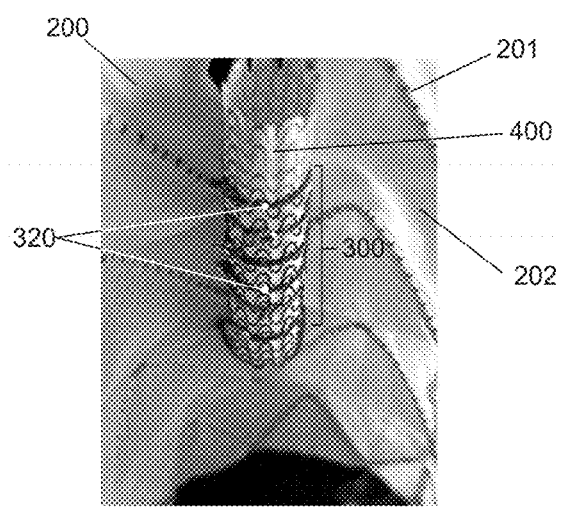
FIG. 4: shows a digital image of an internal part of an endoprosthesis of the system according to the invention.
Figure 5:
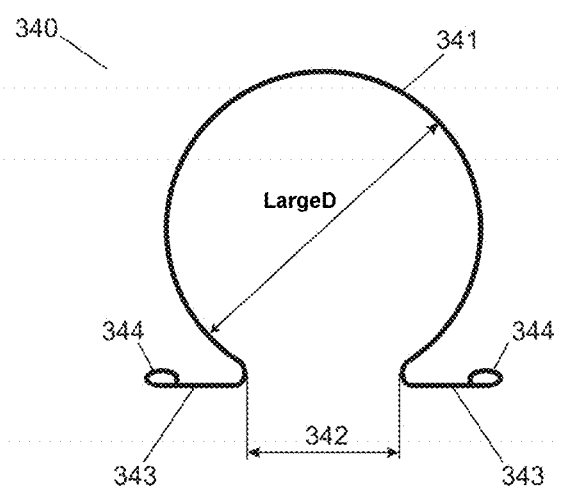
FIG. 5: schematically shows a front view of a rigid fixing and conducting ring, according to the invention.

FIG. 4 shows the endoprosthesis (200) of FIG. 3 with a revascularization endoprosthesis (400) fixed and conducted by the set of fixing and duct elements (300) in the form of flexible fixing and conducting arches (320) according to invention.

The smaller amount of material within the endoprosthesis (200) to form the channel that will fix and connect the vascular endoprosthesis (400) is made evident, and thereby the possible decrease of profile of the endoprosthesis (200) introducer enhancer, diminishing significantly the risks in the implantation in patients with arteries of small caliber.

The set of fixing and duct elements (300) can also be constructed from rigid fixing and conducting rings (340)—see also FIGS. 1b and 1c—, made of biocompatible metallic material suitable for such devices as, for example, but not limited to, nickel and titanium metal alloys, preferably nitinol.

Rigid fixing and conducting rings (340) have a semi-open format, like a horseshoe shape, with a larger segment (341), a lower opening (342) and two side rods (343), wherein the end of each of the side rods (343) and has an arch (344) for the passage of a suture material to attach the rigid fixing and conducting rings (340) to the internal wall of the endoprosthesis (200).

Each rigid fixing and conducting ring (340) has a larger diameter (LargerD) with a size being of 1.8 to 2.2 times, preferably 2 times the size of its lower opening (342). The length of each of the side shafts (343), individually, should not be greater than 70%, preferably 66% of the size of the lower opening (342).

It is to be noted that an endoprosthesis (200) according to the invention may contain flexible fixing and conducting arches (320) or rigid fixing and conducting rings (340) or a combination of the two forms.

Treating Endovascular Aortic Aneurysms or Dissections

According to the description above, it is possible to identify that the system (100), according to the invention, provides a solution for the treatment of aortic aneurysms or dissections in almost all levels of aorta.

The system (100) is suitable both for the treatment of (i) aneurysms or dissections of the thoracic aorta at the level of the aortic arch, where the branches that irrigate the brain and upper limbs emerge, and (ii) thoracic-abdominal aneurysms involving the segments where the visceral branches emerge (celiac trunk, superior mesenteric artery and renal arteries).

The treatment procedure, in general, will always include the construction of 1, 2, 3, or 4 internal channels, starting or ending in the vicinity of one of the fenestrations (210, 220, 230, 240), and by means of the suture to the internal wall of the endoprosthesis (200), or flexible fixing and conducting arches (320) and/or of rigid fixing and conducting rings (340), forming a fixing and conducting structure for the revascularization endoprostheses (400) that will revascularize the visceral vessels during the procedure.

It should be noted that the fenestrations (210, 220, 230, 240) of the system (100) according to the invention are initially occluded by occlusions (215, 225, 235, 245) fixed to (202) of the endoprosthesis (200) by means of sutures (216, 226, 236, 246).

One or more of said sutures (216, 226, 236, 246) will be broken up during the procedure, depending on the number of visceral vessels that need to be under coronary bypass surgery and according to the anatomical position of the same in the patient.

EXAMPLE 1

Thoracic Aneurysm at the Level of the Aortic Arch

In the case of the use of using an endoprosthesis (200) for the treatment of aneurysms of the thoracic aorta at the level of the aortic arch, up to 3 internal channels may be required.

A first channel would begin at 15 mm (below) from the top of the endoprosthesis (200), on the internal anterior face, extending for 25 mm up to its corresponding fenestration (230). As already described above, said first channel may be made either with flexible fixing and conducting arches (320) or with rigid fixing and conducting rings (340), in a number of 5, positioned longitudinally each, and with 8 to 12 mm in larger diameter (LargerD). The fenestration (230) is in this case 7 to 11 mm in diameter and is initially closed by an occlusion (235) of the same material as the coating (202) of the endoprosthesis (200), said occlusion (235) being sutured around the fenestration (230) by a suture (236) made with 6.0 or 7.0 polypropylene cardiovascular suture. Said occluded fenestration (230) is pre-catheterized with hydrophilic guidewire 0.035, which will be used during the procedure to guide the passage of a balloon (not shown) that will disrupt the 6.0 or 7.0 polypropylene cardiovascular suture wire for opening the fenestration (230) if it is necessary to perform the revascularization of the brachiocephalic trunk in the case of the aneurysm of the aortic arch.

After the opening of the fenestration (230) the catheterization of the aortic branch corresponding to this channel is performed, and a revascularization endoprosthesis (400) will be introduced, the usual market one and known in the state of the art, suitable to vascular branch revascularization. This revascularization endoprosthesis (400) will be fixed to the internal part of the endoprosthesis (200) by means of the 5 flexible securing and driving arches (320) or 5 rigid fixing and conducting rings (340), leaving the fenestration (230) and connecting with the corresponding vascular branch.

If said channel it is not necessary for revascularization of any branches, it is sufficient to remove the hydrophilic guidewire 0.035 from the interior of the fenestration (230) which will already be previously occluded by the occlusion (235), thus being without function and without prejudice for the procedure.

A second channel would begin at 25 mm (below) from the top of the endoprosthesis (200), on the internal anterior face, extending for 25 mm up to its corresponding fenestration (220). As already described above, said first channel may be made either with flexible fixing and conducting arches (320) or with rigid fixing and conducting rings (340), in a number of 5, positioned longitudinally each, and with 6 to 8 mm in diameter (Large$_D$). The fenestration (220) is in this case 5 to 7 mm in diameter and is initially closed by an occlusion (225) of the same material as the coating (202) of the endoprosthesis (200), said occlusion (225) being sutured around the fenestration (220) by a suture (226) made with 6.0 or 7.0 polypropylene cardiovascular suture. Said occluded fenestration (220) is pre-catheterized with hydrophilic guidewire 0.035, which will be used during the procedure to guide the passage of a balloon (not shown) that will disrupt the 6.0 or 7.0 polypropylene cardiovascular suture wire for opening the fenestration (220) if it is necessary to perform the revascularization of the left carotid artery in the case of the aneurysm of the aortic arch.

After the opening of the fenestration (220) the catheterization of the aortic branch corresponding to this channel is performed, and a revascularization endoprosthesis (400) will be introduced, the usual market and known to the state of the art, proper to vascular branch revascularization. This revascularization endoprosthesis (400) will be fixed to the internal part of the endoprosthesis (200) by means of the 5 flexible securing and driving arches (320) or 5 rigid fixing and conducting rings (340), leaving the fenestration (220) and connecting with the corresponding vascular branch.

If it is not necessary to use this channel for revascularization of any branch, it is sufficient to remove the hydrophilic guidewire 0.035 from the interior of the fenestration (220) which will already be previously occluded by the occlusion (225), thus being without function and also without prejudice for the procedure.

A third channel would begin at 35 mm (below) from the top of the main endoprosthesis, on the internal anterior face, extending for 25 mm up to its corresponding fenestration (210). As already described above, said first channel may be made either with flexible fixing and conducting arches (320) or with rigid fixing and conducting rings (340), in a number of 5, each positioned longitudinally, and with 6 to 8 mm in large diameter (Large$_D$). The fenestration (210) is in this case 5 to 7 mm in diameter and is initially closed by an occlusion (215) of the same material as the coating (202) of the endoprosthesis (200), said occlusion (215) being sutured around the fenestration (210) by a suture (216) made with 6.0 or 7.0 polypropylene cardiovascular suture. Said occluded fenestration (210) is pre-catheterized with hydrophilic guidewire 0.035, which will be used during the procedure to guide the passage of a balloon (not shown) that will disrupt the 6.0 or 7.0 polypropylene cardiovascular suture wire for opening the fenestration (210) if it is necessary to perform the revascularization of the left subclavian artery in the case of the aneurysm of the aortic arch.

After the opening of the fenestration (210) the catheterization of the aortic branch corresponding to this channel is performed, and a revascularization endoprosthesis (400) will be introduced, the market type and known to the state of the art, proper to vascular branch revascularization. This revascularization endoprosthesis (400) will be fixed to the internal part of the endoprosthesis (200) by means of the 5 flexible securing and driving arches (320) or 5 rigid fixing and conducting rings (340), leaving the fenestration (210) and connecting with the corresponding vascular branch.

If it is not necessary to use this channel for revascularization of any branch, it is sufficient to remove the hydrophilic guidewire 0.035 from the interior of the fenestration (210) which will already be previously occluded by the occlusion (215), thus being without function and also without prejudice for the procedure.

EXAMPLE 2

Thoracic-Abdominal Aneurysm

In the case of the use of using an endoprosthesis (200) for the treatment of thoracic-abdominal aneurysms of the aorta, up to 4 internal channels may be required.

A first channel would begin at 50 mm (below) from the top of the endoprosthesis (200), on the internal anterior face, extending for 25 mm up to its corresponding fenestration (230). As already described above, said first channel may be made either with flexible fixing and conducting arches (320) or with rigid fixing and conducting rings (340), in a number of 5, positioned longitudinally each, and with 6 to 8 mm in large diameter ($Large_D$). The fenestration (230) is in this case 5 to 7 mm in diameter and is initially closed by an occlusion (235) of the same material as the coating (202) of the endoprosthesis (200), said occlusion (235) being sutured around the fenestration (230) by a suture (236) made with 6.0 or 7.0 polypropylene cardiovascular suture. Said occluded fenestration (230) is pre-catheterized with hydrophilic guidewire 0.035, which will be used during the procedure to guide the passage of a balloon (not shown) that will disrupt the 6.0 or 7.0 polypropylene cardiovascular suture wire for opening the fenestration (230) if it is necessary to perform the revascularization of the celiac trunk in the case of thoracic-abdominal aneurysm.

After the opening of the fenestration (230) the catheterization of the aortic branch corresponding to this channel is performed, and a revascularization endoprosthesis (400) will be introduced, the usual market one and known to the state of the art, suitable to vascular branch revascularization. This revascularization endoprosthesis (400) will be fixed to the internal part of the endoprosthesis (200) by means of the 5 flexible securing and driving arches (320) or 5 rigid fixing and conducting rings (340), leaving the fenestration (230) and connecting with the corresponding vascular branch.

If it is not necessary to use this channel for revascularization of any branch, it is sufficient to remove the hydrophilic guidewire 0.035 from the interior of the fenestration (230) which will already be previously occluded by the occlusion (235), thus being without function and also without prejudice for the procedure.

A second channel would begin at 60 mm (below) from the top of the endoprosthesis (200), on the internal anterior face, extending for 25 mm up to its corresponding fenestration (220). As already described above, said first channel may be made either with flexible fixing and conducting arches (320) or with rigid fixing and conducting rings (340), in a number of 5, positioned longitudinally each, and with 6 to 8 mm in large diameter ($Large_D$). The fenestration (220) is in this case 5 to 7 mm in diameter and is initially closed by an occlusion (225) of the same material as the coating (202) of the endoprosthesis (200), said occlusion (225) being sutured around the fenestration (220) by a suture (226) made with 6.0 or 7.0 polypropylene cardiovascular suture. Said occluded fenestration (220) is pre-catheterized with hydrophilic guidewire 0.035, which will be used during the procedure to guide the passage of a balloon (not shown) that will disrupt the 6.0 or 7.0 polypropylene cardiovascular suture wire for opening the fenestration (220) if it is necessary to perform the revascularization of the superior mesenteric artery in the case of thoracic-abdominal aneurysm.

After the opening of the fenestration (220) the catheterization of the aortic branch corresponding to this channel is performed, and a revascularization endoprosthesis (400) will be introduced, the usual market and known to the state of the art, proper to vascular branch revascularization. This revascularization endoprosthesis (400) will be fixed to the internal part of the endoprosthesis (200) by means of the 5 flexible securing and driving arches (320) or 5 rigid fixing and conducting rings (340), leaving the fenestration (220) and connecting with the corresponding vascular branch.

If it is not necessary to use this channel for revascularization of any branch, it is sufficient to remove the hydrophilic guidewire 0.035 from the interior of the fenestration (220) which will already be previously occluded by the occlusion (225), thus being without function and also without prejudice for the procedure.

A third channel and a fourth channel would start at 75 mm (below) the top of the main endoprosthesis on the internal side face, one on each side, extending 25 mm to its corresponding fenestration (210, 240). As already described above, said first channel may be made either with flexible fixing and conducting arches (320) or with rigid fixing and conducting rings (340), in a number of 5, positioned longitudinally each, and with 6 to 7 mm in large diameter ($Large\ _D$). The fenestrations (210, 240) are in this case 5 to 6 mm in diameter and are initially closed by occlusions (215, 245) of the same material as the coating (202) of the endoprosthesis (200), said occlusions (215, 245) sutured around the fenestrations (210, 240) by a suture (216, 246) made with 6.0 or 7.0 polypropylene cardiovascular suture wire. Said occluded fenestration (210, 240) is pre-catheterized with hydrophilic guidewire 0.035, which will be used during the procedure to guide the passage of a balloon (not shown) that will disrupt the 6.0 or 7.0 polypropylene cardiovascular suture wire for opening the fenestration (210, 240) if it is necessary to perform the revascularization of the right and left renal artery in case of thoracic-abdominal aneurysm.

After the opening of the fenestration (210, 240) the catheterization of the aortic branch corresponding to this channel is performed, and a revascularization endoprosthesis (400) will be introduced, the usual market and known to the state of the art, proper to vascular branch revascularization. This revascularization endoprosthesis (400) will be fixed to the internal part of the endoprosthesis (200) by means of the 5 flexible securing and driving arches (320) or 5 rigid fixing and conducting rings (340), leaving the fenestration (210, 240) and connecting with the corresponding vascular branch.

If it is not necessary to use this channel for revascularization of any branch, it is sufficient to remove the hydrophilic guidewire 0.035 from the interior of the fenestration (210, 240) which will already be previously occluded by the occlusion (215, 245), thus being without function and also without prejudice for the procedure.

Corresponding Endoprosthesis

An endoprosthesis (200) according to the invention is a device for endovascular treatment of aortic aneurysms or dissections, especially of aneurysms or dissections located at emergency and/or confluence sites of important arterial branches, which is part of a system (100) according to the invention and comprising:
 (i) a structure (201) and a coating (202) forming a cylindrical or conical, single or bifurcated tubular body, wherein the outer mantle of the coating (202) is provided with fenestrations (210, 220, 230, 240);
 (ii) one or more occlusions (215, 225, 235, 245), fixed to the coating (202) by means of suture (216, 226, 236, 246), reversibly occluding the fenestrations (210, 220, 230, 240), and
 (iii) a set of fixing and duct elements (300), which can be:
  (iii-a) a set of flexible fixing and conducting arches (320), individually fixed to the coating (202); and/or
  (iii-b) a set of rigid fixing and conducting rings (340), individually fixed to the coating (202);

The endoprosthesis (200) according to the invention comprises a structure (201) and a coating (202), the coating (202) being provided with one or more fenestrations (210, 220, 230, 240) displaced in a specific pattern on the external mantle of the coating (202), being open depending on the location of the aneurysm or dissection to be treated.

In a preferred embodiment of the invention, the structure (201) is made of biocompatible metallic material suitable for devices of this kind as, for example, but not limited to, alloys of nickel and titanium, preferably nitinol.

In another embodiment of the present invention, the coating (202) is made from biocompatible synthetic material suitable for such devices as, for example, but not limited to, polytetrafluoroethylene (PTFE) or polyester or the like.

The occlusions (215, 225, 235, 245) reversibly occlude the fenestrations (210, 220, 230, 240) by which they are previously fixed to the coating (202) by means of sutures (216, 226, 236, 246).

In another embodiment of the present invention, the occlusions (215, 225, 235, 245) are made of biocompatible synthetic material and suitable for devices of this kind, such as, but not limited to, polytetrafluoroethylene (PTFE) or polyester or the like, and preferably the same material than the endoprosthesis (200).

In another embodiment of the present invention, the suture is made with cardiovascular suture surgical wire made of, for example, but not limited to the usual and appropriate polyester fibers (as Mersilene®), silk, cotton and other usual and appropriate materials.

The set of fixing and duct elements (300) forms one or more internal channels of the coating (202), being therefore fixed to the internal wall of the coating (202), preferably in the region adjacent one of the fenestrations (210, 220, 230, 240).

The set of fixing and duct elements (300) can be constructed from flexible fixing and conducting arches (320), formed with flexible filamentary material suitable for such procedures. The filamentary material may be cardiovascular surgical suture wire made from, for example, but not limited to, polyester fibers (such as Mersilene®), silk and other usual and suitable materials.

FIG. 2 shows the digital image of an endoprosthesis (200) according to the invention, in which a set of fixing and duct elements (300) in the form of flexible fixing and conducting arches (320), forms an internal channel starting from one of the fenestrations (210) still closed by an occlusion (215) fixed by a suture (216) to the internal wall of the structure (202) of the endoprosthesis (200).

FIG. 3 shows the digital image of the endoprosthesis (200) of FIG. 2 with the occlusion (215) removed.

FIG. 4 shows the endoprosthesis (200) of FIG. 3 with a revascularization endoprosthesis (400) fixed and conducted by the set of fixing and duct elements (300) in the form of flexible fixing and conducting arches (320) according to invention.

The smaller amount of material within the endoprosthesis (200) to form the channel that will fix and connect the vascular endoprosthesis (400) is made evident, and thereby the possible decrease of profile of the endoprosthesis (200) introducer enhancer, diminishing significantly the risks in the implantation in patients with arteries of small caliber.

The set of fixing and duct elements (300) can also be constructed from rigid fixing and conducting rings (340)—see also FIGS. 1b and 1c—, made of biocompatible metallic material suitable for such devices as, for example, but not limited to, nickel and titanium metal alloys, preferably nitinol.

Rigid fixing and conducting rings (340) have a semi-open format, as a horseshoe shape, with a larger segment (341), a lower opening (342) and two side rods (343), wherein the end of each of the side rods (343) and has an arch (344) for the passage of a suture material to attach the rigid fixing and conducting rings (340) to the internal wall of the endoprosthesis (200).

Each rigid fixing and conducting ring (340) has a larger diameter (LargerD) with a size being of 1.8 to 2.2 times, preferably 2 times the size of its lower opening (342). The length of each of the side shafts (343), individually, should not be greater than 70%, preferably 66% of the size of the lower opening (342).

It is to be noted that an endoprosthesis (200) according to the invention may contain flexible fixing and conducting arches (320) or rigid fixing and conducting rings (340) or a combination of the two forms.

Final Considerations

As can be inferred from the description above, the system (100) according to the invention and the corresponding endoprosthesis (200) according to the invention have novel technical effect and inventive activity.

The solution described in this document therefore presents some significant advantages over the state of art devices described.

According to the foregoing description, the system (100) according to the invention provides a solution which, relative to the prior art, has a smaller amount of material inside the endoprosthesis (200) to form the channel that will fix and connect a revascularization endoprosthesis (400) to revascularize a visceral vessel, thereby reducing the profile of endoprosthesis (200), which may reduce implant risks in patients with femoral and iliac arteries of small caliber.

Aortic arch or aortic arch aneurysms may be treated with 1, 2, 3, or 4 patent visceral vessels without the need for modification of the endoprosthesis (200) in its standard configuration, to be used as a "shelf" product.

It will constitute a shelf endoprosthesis (200) with standard configuration and also arrangement of the standard channels, however, with the possibility of treating patients with 1, 2, 3 or 4 visceral vessels or pervious branches, thus increasing the number of patients which can be treated with the same device.

Since less material will be required for making the internal metal and fabric channels, the system (100) according to the invention will also have a lower manufacturing cost with regard to the similar ones of the state of the art.

CONCLUSION

It will be easily understood by those skilled in the art that changes can be made to the present invention without departing from the concepts exposed in the above description. These modifications must be regarded as included in the scope of the present invention. Consequently, the particular embodiments previously described in detail are only illustrative and exemplary and are non-restrictive as to the scope of the present invention, to which the full extent of the appended set of claims and any and all correspondents thereof should be given.

The invention claimed is:

1. An internal duct and fixing system for branches for endovascular endoprostheses for endovascular treatment of aortic aneurysms or dissections, said system comprising:
    an endoprosthesis provided with a plurality of fenestrations;
    one or more occlusions, wherein each occlusion covers one of the plurality of fenestrations and is fixed to the endoprosthesis by a suture, wherein each occlusion is removable from covering one of the plurality of fenestrations; and
    a set of fixing and duct elements that forms one or more internal channels of the endoprosthesis,
    wherein the set of fixing and duct elements are constructed from rigid fixing and conducting rings produced in biocompatible metallic material suitable for such devices.

2. The system, according to claim 1, wherein the rigid fixing and conducting rings have a semi-open format, as a horseshoe, with a larger segment, a lower opening and two side rods wherein the end of each of the side rods and has an arch for the passage of a suture material to secure the rigid fixing and conducting ring to the internal wall of the endoprosthesis wherein the rigid fixing and conducting ring has a larger diameter (LargerD) with a size being of 1.8 to 2.2 times the size of its lower opening (342) in which the length of each of side rods is individually less than 70% of the size of the lower opening.

3. The system, according to claim 1, wherein the endoprosthesis contains a channel formed by the rigid fixing and conducting rings.

4. An endoprosthesis for endovascular treatment of aortic aneurysms or dissections, wherein said endoprosthesis comprises:
    a structure and a coating forming a cylindrical or conical, single or bifurcated tubular body, wherein an outer mantle of the coating is provided with fenestrations;
    one or more occlusions, fixed to the coating by a suture, reversibly occluding the fenestrations; and
    a set of fixing and duct elements, which can be:
    a set of flexible fixing and conducting arches, individually fixed to the coating; and/or
    a set of rigid fixing and conducting rings, individually fixed to the coating; wherein the set of fixing and duct elements forms one or more internal channels of the endoprosthesis.

5. The endoprosthesis according to claim 4, wherein the fenestrations are arranged in a specific pattern in the outer mantle of the coating and are open depending on the location of the aneurysm or dissection to be treated.

6. The endoprosthesis, according to claim 4, wherein the rigid fixing and conducting rings have a semi-open format, as a horseshoe, with a larger segment, a lower opening, and two side rods wherein the end of each of the side rods and has an arch for the passage of suture material to attach the rigid fixing and conducting ring to the endoprosthesis internal wall wherein each rigid fixing and conducting ring has a larger diameter (LargerD) with a dimension of between 1.8 to 2.2 times the size of its lower opening, wherein the length of each of the side rods is, individually, less than 70% of the size of the lower opening.

7. The endoprosthesis, according to claim 4, wherein the endoprosthesis may contain a channel formed by flexible fixing and conducting arches or by rigid fixing and conducting rings or by both combined forms.

8. The system according to claim 1, wherein the set of fixing and duct elements forms the one or more internal channels of the endoprosthesis in the region adjacent to one of the fenestrations.

9. The system according to claim 2, wherein the larger diameter (LargerD) 2 times the size of its lower opening.

10. The system according to claim 2, wherein the length of each of side rods is individually 66% of the size of the lower opening.

11. The endoprosthesis according to claim 4, wherein the set of fixing and duct elements forms one or more internal channels of the endoprosthesis in the region adjacent to one of the fenestrations.

12. The endoprosthesis according to claim 6, wherein the larger diameter (LargerD) 2 times the size of its lower opening.

13. The endoprosthesis according to claim 6, wherein the length of each of side rods is individually 66% of the size of the lower opening.

14. An internal duct and fixing system for branches for endovascular endoprostheses for endovascular treatment of aortic aneurysms or dissections, said system comprising:
    an endoprosthesis provided with a plurality of fenestrations;
    one or more occlusions, wherein each occlusion covers one of the plurality of fenestrations and is fixed to the endoprosthesis by a suture, wherein each occlusion is removable from covering one of the plurality of fenestrations; and
    a set of fixing and duct elements that forms one or more internal channels of the endoprosthesis,
    wherein the set of fixing and duct elements are constructed from flexible fixing and conducting arches, formed with flexible filamentary material suitable for procedures of such kind.

15. An internal duct and fixing system for branches for endovascular endoprostheses for endovascular treatment of aortic aneurysms or dissections, said system comprising:
    an endoprosthesis provided with a plurality of fenestrations;
    one or more occlusions, wherein each occlusion covers one of the plurality of fenestrations and is fixed to the endoprosthesis by a suture, wherein each occlusion is removable from covering one of the plurality of fenestrations; and a set of fixing and duct elements that forms one or more internal channels of the endoprosthesis, wherein the endoprosthesis contains a channel formed by flexible fixing and conducting arches or by rigid fixing and conducting rings or by both combined forms.

\* \* \* \* \*